(12) United States Patent
Bartilucci et al.

(10) Patent No.: US 6,905,654 B2
(45) Date of Patent: Jun. 14, 2005

(54) METHOD AND APPARATUS FOR REDUCING STATIC CHARGES DURING POLYMERIZATION OF OLEFIN POLYMERS

(75) Inventors: Mark Peter Bartilucci, Beaumont, TX (US); Ernest Raymond Davis, Jr., Beaumont, TX (US); Brian J. Egan, Altona (AU); Robert Olds Hagerty, La Porte, TX (US); Per K. Husby, Somerset, NJ (US)

(73) Assignee: Univation Technologies, LLC, Houston, TX (US)

( * ) Notice: Subject to any disclaimer, the term of this patent is extended or adjusted under 35 U.S.C. 154(b) by 261 days.

(21) Appl. No.: 10/360,299

(22) Filed: Feb. 7, 2003

(65) Prior Publication Data

US 2003/0133839 A1 Jul. 17, 2003

Related U.S. Application Data

(62) Division of application No. 09/802,090, filed on Mar. 8, 2001, now Pat. No. 6,548,610.
(60) Provisional application No. 60/239,012, filed on Oct. 6, 2000.

(51) Int. Cl.[7] ............................................. G10N 15/06
(52) U.S. Cl. ...................................... 422/68.1; 422/131
(58) Field of Search ............................... 422/68.1, 131

(56) References Cited

U.S. PATENT DOCUMENTS

| | | | |
|---|---|---|---|
| 4,803,251 A | 2/1989 | Goode et al. | 526/59 |
| 4,855,370 A | 8/1989 | Chirillo et al. | 526/74 |
| 5,346,304 A | 9/1994 | Kleinhans | 366/219 |
| 5,391,657 A * | 2/1995 | Song et al. | 526/74 |
| 5,405,922 A | 4/1995 | DeChellis et al. | 526/68 |
| 5,436,304 A | 7/1995 | Griffin et al. | 526/68 |
| 5,541,270 A | 7/1996 | Chinh et al. | 526/68 |
| 5,648,581 A | 7/1997 | Kubo et al. | 585/501 |
| 5,733,510 A | 3/1998 | Chinh et al. | 422/143 |
| 6,001,938 A | 12/1999 | Chinh et al. | 526/68 |
| 6,008,662 A | 12/1999 | Newton et al. | 324/724 |
| 2002/0047712 A1 * | 4/2002 | Weick et al. | 324/453 |

FOREIGN PATENT DOCUMENTS

| | | |
|---|---|---|
| DE | 2800157 A1 | 7/1978 |
| EP | 0326430 A1 | 8/1989 |
| EP | 0635724 A2 | 1/1995 |

* cited by examiner

*Primary Examiner*—William K. Cheung
(74) *Attorney, Agent, or Firm*—Osborne K. McKinney; Kevin M. Faulkner

(57) ABSTRACT

The present invention relates to a method and apparatus for controlling static charges in a fluidized bed olefin polymerization reactor. Static charges which develop in the polymer products are measured and, if they fall outside a predetermined range, static charge control agents are introduced into the reactor. By controlling the static charges in the reactor, sheeting and drooling can be controlled.

7 Claims, 2 Drawing Sheets

METHOD AND APPARATUS FOR REDUCING STATIC CHARGES DURING POLYMERIZATION OF OLEFIN POLYMERS

RELATED APPLICATION DATA

The present application is a divisional of U.S. patent application Ser. No. 09/802,090 filed Mar. 8, 2001, now issued as U.S. Pat. No. 6,548,610, which claims benefit of U.S. Provisional Application Ser. No. 60/239,012 filed Oct. 6, 2000, and is herein incorporated by reference.

FIELD OF THE INVENTION

The present invention relates to a method and apparatus for controlling static charges in a fluidized bed olefin polymerization reactor. By controlling the static charges in the reactor, sheeting and drooling can be controlled.

BACKGROUND OF THE INVENTION

One of the major advances in olefin polymerization technology has been the development of commercially useful metallocene based catalyst systems. Among other advantages, metallocene catalysts allow the production of polyolefins with unique properties such as narrow molecular weight distribution. These properties in turn result in improved structural performance in products made with the polymers such as greater impact strength and clarity in films.

While metallocene catalysts have yielded polymers with improved characteristics, they have presented new challenges when used in traditional polymerization systems. One such area has been in the control of "sheeting" and the related phenomena "drooling" when metallocene catalysts are used in fluidized bed reactors such as those described in U.S. Pat. Nos. 5,436,304 and 5,405,922. By "sheeting" is meant the adherence of fused catalyst and resin particles to the walls of the reactor. The sheets will eventually dislodge from the wall and, if the sheets are large enough, they can result in reactor plugging. "Drooling" or dome sheeting occurs when sheets of molten polymer form on the reactor walls, usually in the expanded section or "dome" of the reactor, and flow along the walls of the reactor and accumulate at the base of the reactor. This can result in plugging of the distributor plate in the reactor and loss of fluidization.

In commercial reactors, sheets can vary widely in size, and are usually about 0.6 to 1.3 cm thick and are from 0.3 to 2.0 meters long, with a few even longer. They can have a width of about 7 cm to more than 45 cm. The sheets have a core composed of fused polymer which is oriented in the long direction of the sheets, and their surfaces are covered with granular resin which is fused to the core. The edges of the sheets can have a hairy or stringy appearance from strands of fused polymer.

It has been found that there exists a strong correlation between polymer sheeting and drooling and the presence of an excess of static charges, either positive or negative, in the reactor during polymerization. This is evidenced by sudden changes in static levels followed closely by deviation in temperature at the reactor wall. These temperature deviations are either high or low. Low temperatures indicate particle adhesion to the reactor causing an insulating effect from the bed temperature. High deviations indicate reaction taking place in zones of limited heat transfer. Following this, disruption in fluidization patterns is generally evident, such as, for example, catalyst feed interruption, plugging of the product discharge system, and the occurrence of fused agglomerates (sheets) in the product.

Various methods for controlling sheeting have been developed. These often involve monitoring the static charges near the reactor wall in regions where sheeting is known to develop and introducing a static control agent into the reactor when the static levels fall outside a predetermined range. For example, U.S. Pat. Nos. 4,803,251 and 5,391,657 disclose the use of various chemical additives to a fluidized bed reactor to control static charges in the reactor. A positive charge generating additive is used if the static charge is negative, and a negative charge generating additive is used if the static charge is positive. The static charge in the reactor is measured at or near the reactor wall at or below the site where sheet formation usually occurs, using static voltage indicators such as voltage probes or electrodes.

The prior art, such as that disclosed in U.S. Pat. Nos. 4,803,251 and 5,391,657, teaches that static plays an important role in the sheeting process with Ziegler-Natta catalysts. We have found that static also plays an important role in sheeting and drooling with metallocene catalyst. When the static charge levels on the catalyst and resin particles exceed certain critical levels, the particles become attached by electrostatic forces to the grounded metal walls of the reactor. If allowed to reside long enough on the wall under a reactive environment, excess temperatures can result in particle fusion and melting, thus producing the sheets or drools.

The principal cause for static charge generation in the reactor is frictional contact of dissimilar materials by a physical process known as the triboelectric effect. In the gas phase, polymer production reactors, the static is generated by frictional contact between the catalyst and polymer particles and the reactor walls. The frictional contact causes a flow of electrical charges from the walls of the grounded metal reactor to or from the polymer and catalyst particles in the fluid bed. The charge flow can be measured by employing static probes. Typical charge flows (currents) are of magnitude 0.1 to 10 microamperes per square meter of reactor surface area. Although these currents are very low, relatively high levels of electrical charge can accumulate over time in the reactor. This accumulation is enabled by the highly insulating characteristics of the polymer and catalyst particles.

The frictional electrification of the polymer and catalyst particles can be strongly influenced by the type of polymer that is being produced. In particular, the polymer molecular weight has a strong effect, with higher molecular weight polymers being more prone to developing high levels of static charge. Static charging in the fluid bed is also strongly influenced by the presence of minute quantities of static charge inducing impurities.

When sufficiently high levels of charge or charge accumulation becomes large enough, the frictional electrification of the polymer and catalyst particles can be strongly influenced by the type of polymer that is being produced. In particular, the polymer molecular weight has a strong effect, with higher molecular weight polymers being more prone to developing high levels of static charge. Static charging in the fluid bed is also strongly influenced by the presence of minute quantities of static charge inducing impurities.

For conventional catalyst systems such as traditional Ziegeler-Natta catalysts or Chromium-based catalysts, sheet formation usually occurs in the lower part of the fluidized bed. For this reason, the voltage indicators have traditionally been placed in the lower part on the reactor. For example, in U.S. Pat. No. 5,391,657, the voltage indicator was placed near the reactor distributor plate. See also U.S. Pat. No.

4,855,370. The indicators were also placed close to the reactor wall, normally less than 2 cm from the wall.

There are two types of static indicators (or probes) described in the prior art, the "voltage probe" (U.S. Pat. No. 4,855,370) and the "current probe" (U.S. Pat. No. 5,648,581 and U.S. Pat. No. 6,008,662). Both types of probes are similar in that they measure electrical characteristics of the fluidized bed near the reactor wall. The current probe measures the electrical current flowing from a metal electrode (probe tip) by the frictional contact of the resin and catalyst particles. It is intended to provide a single-point measurement of the surface current flowing from the much larger metal walls of the reactor to the fluid bed.

The voltage probe consists of a simple metal electrode connected to an external voltage measuring device of high resistance. Typical values of the resistance are of the order of 100 giga-ohms ($10^{11}$ ohms). The authors of U.S. Pat. No. 4,855,370 mistakenly considered the readings from these probes to be an indication of the voltage within the fluid bed, as generated by the static charge. A more recent patent (U.S. Pat. No. 6,008,662) teaches that, despite the high resistance, the voltage probes actually measure the surface current. That is, the "voltage" indicated on the probes of U.S. Pat. No. 4,855,370 is actually just the product of the surface current times the resistance. Both types of probes are therefore functionally equivalent. They both measure surface current. As indicated above, typical values of surface current are on the order of 1 to 10 microamperes per square meter of reactor surface area.

It has been found that for metallocene catalyst systems, the use of a traditional voltage indicator has been ineffective in predicting the static charge in the fluidized bed and thereby reduces their effectiveness in preventing sheeting and/or drooling. This was completely unexpected based on the inventor's experience with olefin polymerizations in fluidized bed reactors and the teachings of the prior art. It is believed that this is due to the presence of a large amount of particle fines in the reactor. These fines accumulate at or near the reactor walls and hence near the static probes typically used in a fluidized bed reactor. These fines appear to prevent the polymer particles in the fluidized bed from transferring their charge to the static probes.

A proposed solution to the problem was to measure the static charge in the fluidized bed itself. To accomplish this, a needle probe was extended from the reactor wall into the heart of the fluidized bed. This probe failed to properly measure the static charge in the bed and sheeting occurred. The fines which coated the prior art probes also coated the needle probe, rendering it ineffective.

Thus it is apparent that a new method for determining that static charge in a fluidized bed reactor is needed, especially for use with metallocene catalyst systems.

SUMMARY OF THE INVENTION

The present invention provides a method for controlling the static charge in a fluidized bed reactor and thereby controlling sheeting or drooling. This is accomplished by measuring the static charge within the fluidized bed of a reactor and thereby determining if static control agents need to be added and the type of static control agents which must be added.

The invention involves taking a sample of the polymer product exiting the reactor and determining the static charge of the sample. In this embodiment, a polymer sample is taken from the exit stream of the reactor and is placed directly into a device for measuring the static charge of the polymer sample, e.g., a Faraday drum.

The static charged measured can then be compared with a range of acceptable static charge values. If the measured static charge falls outside the predetermined range of acceptable values, a static control agent is added to the reactor. The nature and amount of the static control agent will depend upon the polarity and size of the static charge measured as well as the type of catalyst used. For example, if the measured charge has a negative polarity, a positive charge inducing static control agent is used. Likewise, if the static charge is positive, a negative charge inducing static control agent is used. The amount used should be the least amount necessary to reduce the static charge in the reactor without negatively impacting the polymerization reaction. Specific static control agents useful in the practice of this invention are well known to those in the art.

DETAILED DESCRIPTION OF THE INVENTION

Figure 1:
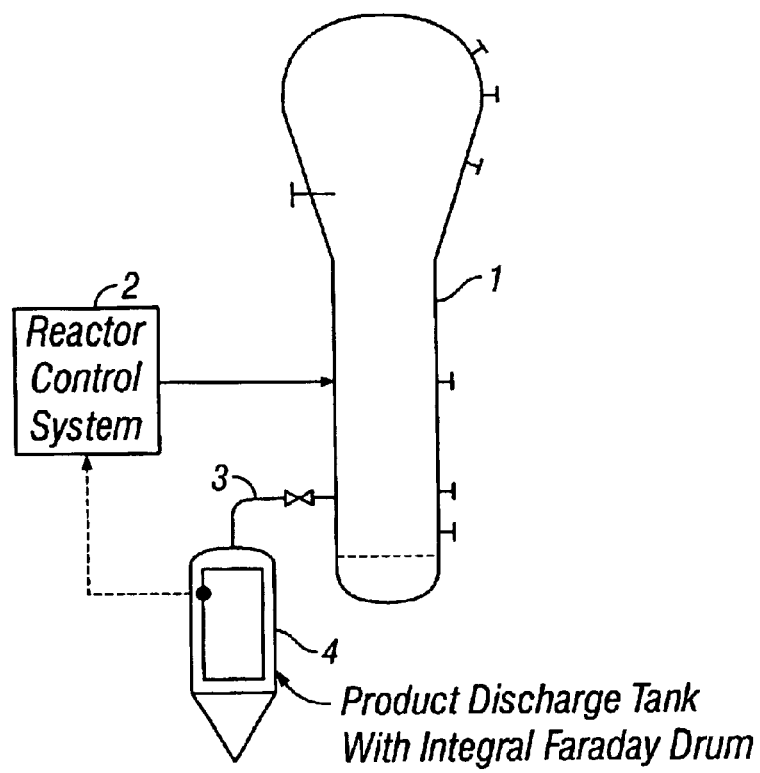
FIG. 1 is a schematic diagram of a gas phase reactor showing the static control method of the present invention in contrast to that of the prior art.

Sheeting and drooling can be substantially reduced and in some cases eliminated by controlling static charges in the fluidized bed. In general, sheeting is evidenced by one or more reactor thermocouples registering a temperature excursion of up to 20° C. above the temperature of the fluidized bed. The static charged level for sheeting is not a fixed value, but is a complex function dependent upon variables including resin sintering temperature, operating temperature, drag forces in the fluidized bed, resin particle size distribution and recycle gas composition. Generally, the closer the charge value is to zero, the less likely sheet formation will occur.

As discussed above, especially for fluidized bed processes where metallocene catalyst systems are used, it is preferable to measure the static charge within the bed, not at the reactor wall. Thus it is necessary to employ a method for measuring static charges that exist in the fluidized bed.

While the present invention is useful in many types of fluidized bed reactors, it is most useful in what are often called "gas phase reactors" such as those described in U.S. Pat. Nos. 5,346,304; 5,405,922; and 4,803,251; the teachings of which are hereby incorporated by reference for U.S. practice. An alternative design of a "gas phase reactor" is that found in U.S. Pat. Nos. 5,733,510; 5,541,270; and 6,001,938; the teachings of which are incorporated by reference for U.S. practice.

The present invention provides a method for controlling the static charges in the fluidized bed reactor and thereby controlling sheeting and drooling. It involves the steps of determining the static charge of the particles in the fluidized bed reactor; comparing the measured static charge with a predetermined range of static values; and, if the measured charge falls outside the predetermined range of static charge values, adding a static control agent to the reactor.

With a reaction in progress, changes in static voltage levels from neutral to positive can be counteracted by feeding a negative charge generating chemical additive to the reactor during polymerization using a feeding means such as, for example, through a hopper or adding the additive to the ethylene stream. Alternatively, changes in static voltage levels from neutral to negative can be counteracted by feeding a positive generating additive to the reactor during polymerization. Mixtures of positive and negative generating inorganic additives can also be introduced in the reactor as a single physical mixture via a hopper; each delivered independently via two feeders or hoppers; or as a chemically-bonded entity such as a refractory oxide support for the catalyst. If this is not performed, impending agglomerate formation will likely create a process upset. Care must be exercised to avoid excessive chemical additives which can result in unwanted static voltage levels. The positive and negative charge generating inorganic chemical additives can be added or fed to the system in a variety of ways known to those skilled in the art. One such feeding arrangement can include, for example, the use of one or more feeders at a point below or above the distributor plate of the reactor.

The invention involves measuring the static charge of the polymer particles as they exit the reactor. During the polymerization process, polymer particles are formed in the fluidized bed in the reactor. These particles tend to rub against the walls of the reactor thereby acquiring a static charge. Due to their highly insulating nature the polymer particles tend to retain the static charge, with the charge dissipating only after a significant amount of time passes. Thus, the polymer particles exiting the reactor will have essentially the same charge as the particles in the reactor. This allows measurement of the charge in the fluidized bed by measuring the charge of the polymer particles exiting the reactor. As will be shown in the examples below, this is a better indication of the actual charge in the fluidized bed than the use of surface probes taught by the prior art.

Referring to FIG. 1, as the polymer exits the reactor, 1, it enters a discharge stream, 3, All or part of the exiting polymer is then captured and placed into a device for measuring the static charge the polymer and the weight of the polymer in the device. In the preferred embodiment, the device for measuring the static charge of the polymer is a Faraday drum or cage, 4, described more fully below. The static charge measuring device then relays a signal to a reactor control system, 2, which compares that static charge measured for the polymer sample with a predetermined range of acceptable static charge values. If the measured static charge falls outside the predetermined range of acceptable static charge values, the appropriate static control agent is added to the reactor.

Figure 2:
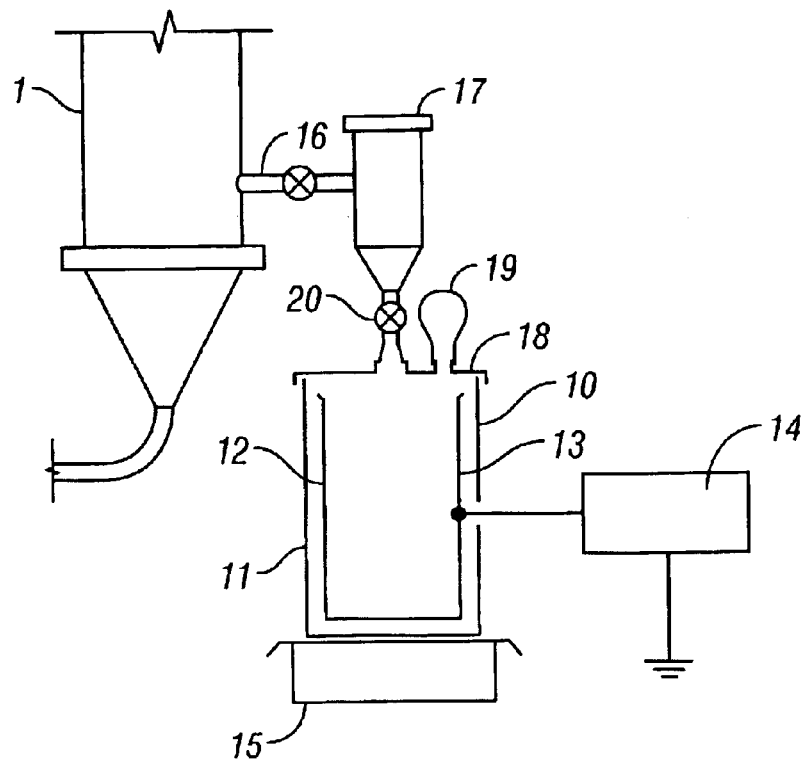
FIG. 2 is a diagram of a Faraday drum system useful in the practice of the method of the present invention.

Referring to FIG. 2, a device for measuring the static charge of the polymer exiting a fluidized bed reactor is shown. The device comprises a Faraday drum or cage, 10, which in turn comprises an external shielding drum, 11, an inner drum, 12, and an insulating layer, 13, between the drums such that there is no electrical contact between the two drums. A means for measuring current flow, 14, is attached to the wall of the inner drum, 12, in order to measure the static charge induced by the polymer when it enters in the inner drum, 12. The means for measuring the current flow may also be associated with a means for integrating the current over time. The Faraday drum, 10, rests on a scales, 15, so that the weight of any polymer added to the drum can be determined.

The inner, 12, and external shielding drum, 10, are made of an electrically conductive material, e.g., metal. In the preferred embodiment, the drums are made of a metal selected from the group comprising stainless steel, aluminum, copper and carbon steel, with stainless steel most preferred.

The external shielding drum, 10, which is grounded, acts to block external electric fields and charges from inducing a charge on the inner drum, 12. In this way, the charge measured by the inner drum, 12, is only that charge induced in it by the polymer sample. Any charge induced in the external shielding drum, 10, from the environment is isolated from the inner drum by the insulating layer. This layer can comprise any suitable insulating material, e.g., Teflon™, or can comprise an air pocket between the inner and outer drums as long as the inner and outer drums are electrically isolated from each other.

The Faraday drum is closed with a drum cover, 18. As shown in FIG. 2, the cover is equipped with a vent covered with a sock filter, 19. This allows the release of pressure from the Faraday drum while trapping the polymer sample inside. Other possible vent and filter arrangements useful in the practice of the invention are known to those skilled in the art.

The Faraday drum represents an application of a fundamental measurement technique named after Michael Faraday, a British physicist and chemist (1791–1867). The system operates on the principal of displaced current. Because the inner drum of the Faraday system is connected to ground through a low resistance current measuring device, the voltage on the inner drum must be zero. When charged resin and catalyst particles enter the Faraday drum, an electrical current is displaced from the Faraday drum through a current measuring device to ground, as required to keep the overall system voltage zero. The amount of charge displaced to ground is equal and opposite to the charge that enters the drum with the resin and catalyst particles. The current flow is recorded and integrated over the time period that the particles are introduced to the system to provide a quantitative measurement of the charge.

In practice, the actual measurement taken is the current that flows from ground to the drum, which is opposite in sign to the current flow from the drum to ground. In effect, the current meter is connected backwards to provide a sign inversion to the measurement. In this way, the measured current, integrated over time, is exactly equal to the charge that enters the system, both in magnitude and sign.

The preferred means of measuring the current flow is with an electrometer, such as a Keithley Model 610C. These devices provide the dual capability of measuring and integrating the current as required by the Faraday technique. Other means to measure and integrate the current can be employed, as known by those skilled in the art. For example, the current can be measured with a simple current meter (ammeter), with the readings recorded and digitally integrated over time to provide the required charge measurement.

As the polymer exits the reactor, 1, it flows through a conduit, 16, to a product discharge tank, 17. Depending upon the size of the reactor, 1, the size of the product discharge tank, 17, and the size of the Faraday drum, 10, all of the polymer in the tank may be used to determine the static charge or only a portion may be used. From the product discharge tank, 17, at least a portion of the polymer flows through a second conduit 20, into the inner drum, 12, of the Faraday drum, 10. As the polymer enters the inner drum, 12, the static charge on the polymer induces an opposite charge in the inner drum. The charge induced on the inner drum, 13, causes a flow of current from the ground, through the electrometer, 14, to the inner drum, 13, until an overall potential of zero is reached. The current flow is then recorded by the means for measuring current flow, 14, and integrated over the time the polymer sample is transferred from the product discharge tank, 17, to the Faraday drum. The charge on the inner drum is taken to be equal to the integrated current, both in size and polarity. The weight of the resin transferred into the Faraday drum from the polymer discharge tank is also measured and the final result of both measurements is displayed in units of micro-coulombs per kilogram of polymer.

In addition to the size of the static charge in the reactor, the polarity of the charge must also be determined. This is important because the polarity will determine the nature of the static control agent used to reduce the static charge in the reactor.

By static control agent we mean a chemical composition which when introduced into the fluidized bed reactor reduces the static charge in the fluidized bed. The specific static control agent used will depend upon the nature of the static charge. For example, if the static charge is negative, then static control agents such as positive charge generating compounds such as MgO, ZnO, $Al_2O_3$ and CuO can be used. In addition, alcohols such as methanol, oxygen and nitric oxide can be used to control negative static charges. See, e.g., U.S. Pat. No. 4,803,251 and U.S. Pat. No. 4,555,370. For positive static charges, negative charge generating inorganic chemicals such as $V_2O_5$, $SiO_2$, $TiO_2$, $Fe_2O_3$ can be used. In addition, water or ketones containing up to 7 carbon atoms can be used to reduce a positive charge. When metallocene catalysts are used in the fluidized bed polymerization process, alternative static control agents such as aluminum stearate are often used. Again, the static control agent used is selected for its ability to receive the static charge in the fluidized bed without adversely affecting productivity.

The above are merely illustrations of static control agents useful in the practice of the invention. Other static control agents useful in the practice of the invention are well known to those in the art. Regardless of which agent is used, care should be exercised in selecting an appropriate static control agent to avoid introduction of poisons into the reactor. In addition, the smallest amount of the agent necessary to bring the static charge into alignment with the desired range should be used.

The present invention works best when a discrete sample or batch of polymer is introduced into a Faraday drum and an electrostatic charge is induced in the drum. Present gas phase polymerization processes are ideally suited for this type of measurement.

In the typical gas phase reactor, finished polymer particles are recovered from the reactor in batches and are transported into a polymer discharge tank similar to that described above. In an alternative embodiment, the product discharge tank itself can be converted into a Faraday drum. In this embodiment, the product discharge tank is fitted with a liner comprising an insulating layer and an inner drum. The inner drum is connected to an electrometer in the manner described above. The walls of the existing discharge tank act as the outer shield drum. In this manner, an existing product discharge system can be readily modified to take advantage of the present invention.

Another embodiment allows for the continuous discharge of polymer. In this embodiment, samples of polymer are taken from the product discharge stream and static charge measurements are made on the sample. Samples of polymer can be taken from a discharge stream by a number of different methods known to those in the art, including settling legs, scoops, and the like.

The following examples illustrate the effectiveness of the invention.

EXAMPLES

Examples 1–5

Commercial Reactor Trials

In examples 1 through 5, the results of five commercial reactor runs are reported. The same reactor system was used in each case. The fluid bed section of the reactor was 4.4 meters in diameter and 13.5 meters in height. A metallocene catalyst system was used to make an ethylene-hexene copolymer having a target density of 0.915 to 0.918 g/cc and a target melt index of 1.2 to 3.2 g/10 min. The catalyst used was bis (n-butylcyclopentadienyl) zirconium dichloride with methyl aluminoxane supported on Davidson 952-1863 silica. In each case, the reaction was started and operated for only 17 to 31 hours before problems were encountered with sheeting. The sheeting caused a sudden loss of fluidization and/or poor temperature control, which forced the operators to terminate the reaction with an injection of carbon monoxide "kill" gas. In each case, the reactors had to be opened and the sheets physically removed. In contrast, a normal fluidized bed reactor run will normally last from 3 to 6 months. Table 1 reports the results of the five plant trials and the reason for the premature shutdowns.

With the exception of example 1, the static probes indicated no significant deviation from neutral, yet the reactor experienced poor temperature control and in three cases sudden defluidization due to sheeting. Thus the static probes were totally ineffective in preventing the development of sheeting or drools. These same probes have been effective in detecting conditions which lead to sheeting when more traditional catalysts were used.

TABLE 1

| Example No. | 1 | 2 | 3 | 4 | 5 |
| --- | --- | --- | --- | --- | --- |
| Bed Temperature, (° C.) | 84 | 82 | 82 | 75 | 80 |
| Catalyst Productivity (g/g) | 3700 | 2400 | 3000 | 3000 | 2500 |
| Ave. Particle Size, (in.) | 0.028 | 0.029 | 0.034 | 0.027 | 0.028 |
| Fines < 120 mesh, (wt. %) | 2.90 | 1.60 | 2.07 | 2.72 | 0.30 |
| Static Probe Readings (ηA) | −1 to −2 | −8 to 0 | −1 to +1 | −1 to +1 | +0.0 to +1.5 |

TABLE 1-continued

| Example No. | 1 | 2 | 3 | 4 | 5 |
|---|---|---|---|---|---|
| Bed Skin Temps. at 2–6' level, (° C.) | −10 to −15 | −10 to −5 | −10 to −5 | −4 to −6 | −10 to −15 |
| Run Duration (hours) | 31 | 24 | 24 | 17 | 20 |
| Reason for Run Termination | poor reactor temp. control | Sudden defluidization | sudden defluidization | skin temp. activity | sudden defluidization |
| Massive Chunk | thick, folded sheets in PPV | Thick, folded sheets | thick, folded sheets | none | thick, folded sheets |
| Individual Drools | none | Many on plate, one in dome | several | one each on plate & dome | one large in dome |

*Catalyst productivity = g catalyst/g polymer

Examples 6 through 9.

A series of four experiments were carried out using a pilot plant reactor. The fluid bed, pilot plant reactor was operated substantially in the manner disclosed by Nowlin et al., U.S. Pat. No. 4,481,301. The reactor was 0.36 meters in diameter and it was capable of producing up to 25 kg/hr. of resin. A steady-state reaction was obtained by continuously feeding catalyst and reactant gases (ethylene and 1-hexene) to the reactor while also continuously withdrawing. polymer product from the reactor. The same catalyst system was used as was used in the preceding examples with the exception the catalyst in example 9 was prepared in a pilot plant rather than in a commercial facility. In addition, a Faraday drum static charge detector as described above was used to determine the static charge of the polymer exiting the reactor. Table 2 summarizes the data developed during these experiments.

TABLE 2

| Example No. | 6 | 7 | 8 | 9 |
|---|---|---|---|---|
| Result | Drools | Drools | Drools | No drools or sheets |
| Static Probe (η-amps) | −1.12 | −0.49 to −0.87 | −0.58 to −0.93 | −0.57 to −0.70 |
| Faraday Drum (μ-coul/kg) | −21.1 | −7.0 to −24.6 | −13.6 to −24.8 | −3.4 to −5.8 |

Figure 3:
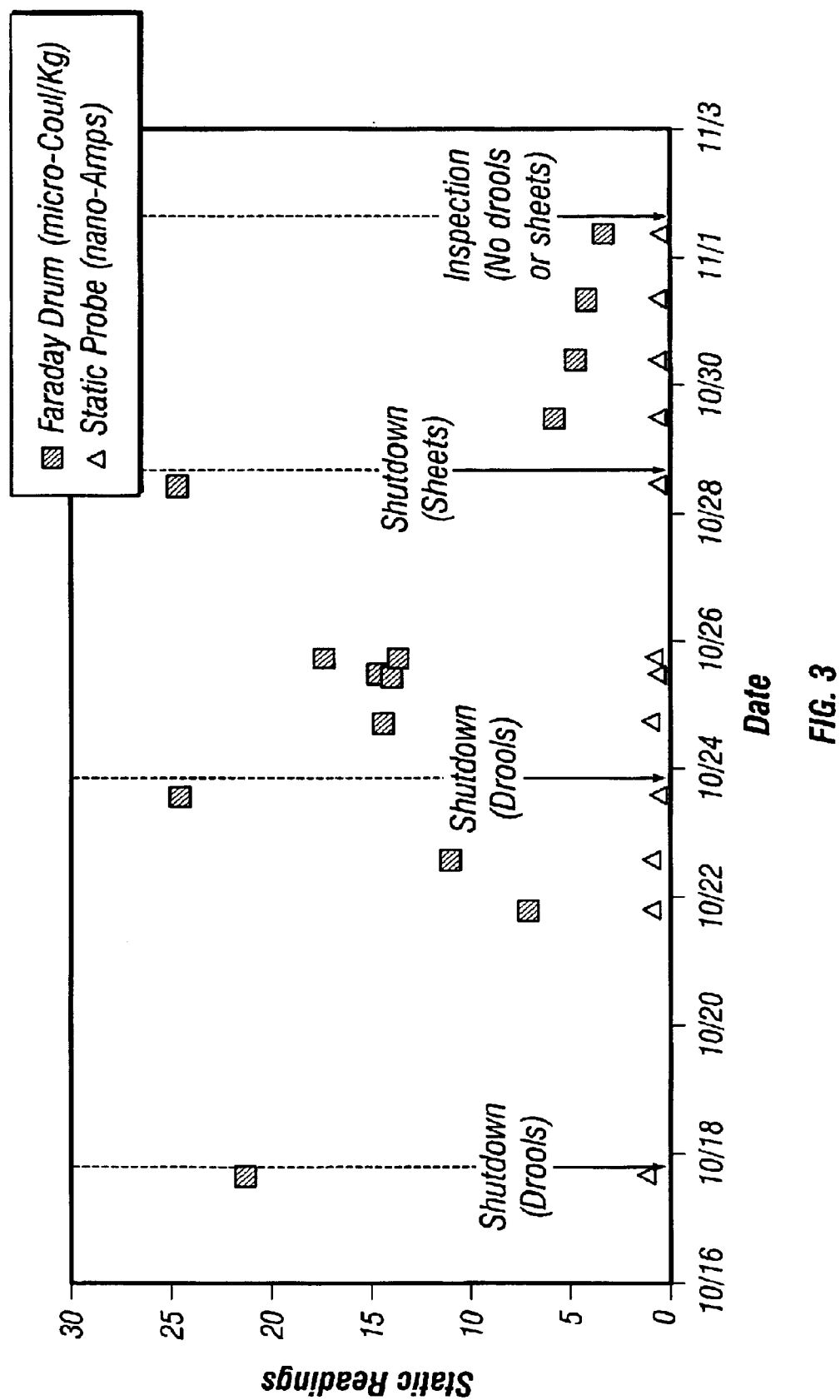
FIG. 3 is a plot of four pilot plant runs comparing the static charge measurements for a static probe of the prior art and the Faraday drum system of the present invention.

Again, as with the commercial reactor runs, the static probes showed no significant change throughout the tests, yet in three of the runs, there was significant drooling. With the Faraday drum, however, significant changes in the static charge were observed over the course of the run. It was noted that when the drum readings exceeded −20Φ-coul/kg, drooling or sheeting occurred. As shown in example 9, when the static charge was maintained at a lower level, e.g., 3.4 to −5.8Φ-coul/kg, no drooling occurred. A graphic demonstration of this relationship can be seen in FIG. 3.

The examples above demonstrate the effective uses of the present invention in measuring the actual static charge within the reactor. In the examples where sheeting or drooling occurred, the Faraday drum system showed a significant deviation from a neutral charge whereas the traditional static probes registered an essentially neutral condition. Thus measuring the static charge with the Faraday drum is an effective way of determining when sheeting or drooling is likely to occur.

While the above examples were conducted using metallocene-based catalysts, the present invention may also be used with traditional catalysts such as Ziegeler Natta catalyst systems or Chromium-based systems.

What is claim is:

1. An apparatus for measuring static charges in a fluidized bed olefin polymerization reactor comprising:

(a) a Faraday drum;

(b) a conduit for transporting a polymer sample from the reactor to the Faraday drum;

(c) a means for measuring electric current flow connected to said Faraday drum to measure the static charge of the polymer sample in the Faraday drum.

2. The apparatus of claim 1 further comprising a means for integrating the electric current flow over time.

3. The apparatus of claim 1 wherein said means for measuring electric current flow comprises an electrometer.

4. The apparatus of claim 1 wherein said Faraday drum comprises an inner drum, an outer shielding drum and an insulating layer between said inner and outer drums.

5. The apparatus of claim 2 wherein said electrometer is connected to said inner drum.

6. The apparatus of claim 1 further comprising a scale to measure the weight of polymer in said Faraday drum.

7. The apparatus of claim 2 wherein said outer shielding drum comprises a product discharge tank.

* * * * *